United States Patent [19]

Blatchford et al.

[11] E Patent Number: Re. 31,673

[45] Reissued Date of Patent: Sep. 18, 1984

[54] STABILIZED ARTIFICIAL KNEE MECHANISM

[75] Inventors: Brian G. Blatchford, Basingstoke; Paul A. Tucker, Yeovil, both of England

[73] Assignee: Chas. A. Blatchford & Sons Ltd., Basingstoke, England

[21] Appl. No.: 354,232

[22] Filed: Mar. 2, 1982

Related U.S. Patent Documents

Reissue of:

[64] Patent No.: 4,206,519
Issued: Jun. 10, 1980
Appl. No.: 931,945
Filed: Aug. 8, 1978

[51] Int. Cl.[3] ..... A61F 1/04

[52] U.S. Cl. ..... 3/27; 188/336

[58] Field of Search ..... 3/26, 27, 28, 2; 188/336, 339

[56] References Cited

U.S. PATENT DOCUMENTS 1,093,330 4/1914 Hutchinson .
2,519,226 8/1950 Coe, Jr. .
2,551,537 5/1951 Havens .
2,885,687 5/1959 Kelsey .
3,694,823 10/1972 May .
3,863,274 2/1975 Glabiszewski ..... 3/27

FOREIGN PATENT DOCUMENTS 2023040 8/1971 Fed. Rep. of Germany .
598291 2/1948 United Kingdom .
779087 7/1957 United Kingdom .
897811 5/1962 United Kingdom .
1221778 2/1971 United Kingdom .
645649 2/1979 U.S.S.R. ..... 3/26

*Primary Examiner*—Clifford D. Crowder
*Attorney, Agent, or Firm*—Cushman, Darby & Cushman

[57] ABSTRACT

An artificial leg has a stabilized knee mechanism, that is, a mechanism which resists flexion of the leg when the latter is under load. The leg has upper and lower leg components, for example thigh and shin, and the knee mechanism includes a hollow brake drum with a brake shoe inside it. The drum is connected to the thigh and the shoe to the shin. The shoe frictionally engages the inner surface of the drum to resist flexion of the leg when it is under load.

12 Claims, 5 Drawing Figures

STABILIZED ARTIFICIAL KNEE MECHANISM

Matter enclosed in heavy brackets [ ] appears in the original patent but forms no part of this reissue specification; matter printed in italics indicates the additions made by reissue.

FIELD OF THE INVENTION

This invention relates to an artificial leg having a stabilised knee mechanism. In this specification the expression "stabilised knee mechanism" is to be construed as a mechanism which resists flexion of the leg when the latter is under load, i.e. with it is bearing at least some of the weight of the amputee.

DESCRIPTION OF THE PRIOR ART

British Pat. No. 779,087 (B. G. Blatchford) disclosed a stabilished knee mechanism having a drum fixed to the shin of the leg and a flexible brake band embracing the drum and connected to the thigh of the leg. This mechanism allows some relative movement (other than rotating movement) between the thigh and the shin, and is arranged so that when the leg is under load the shin and the thigh move towards each other and cause the brake band to tighten around the drum. The brake band includes a layer of friction material which grips the drum to resist flexion of the leg. Other mechanisms are disclosed in British Pat. Nos. 598,219; 897,811; and 1,221,778. The mechanism disclosed in British Pat. No. 779,087 has been successfully used for many years in legs for patients with above-knee amputations, but its size is such that it can only be accommodated if the stump is shorter than a given length corresponding to the minimum required clearance for the mechanism between the end of the stump and the knee centre. In order to accommodate a longer stump, a more compact mechanism is needed. The extent by which the size of this and other known mechanisms can be effectively reduced is limited by the need for sufficient braking friction area, by the need for a unit which is strong and reliable, and by the presence of the brake band and its associated components outside the brake drum.

The mechanism disclosed in British Pat. No. 779,087 also has the disadvantage that it is unsuitable for incorporation in an endoskeletal leg, i.e. a leg having a continuous outer covering. The anchorage points of the brake band are external to the diameter of the drum and necessarily at the front of the knee where, if an endoskeletal covering is being used, there is the least amount of space available.

It is thus an object of this invention to provide an artificial leg with a stabilised knee mechanism which is more compact in construction than known mechanisms.

SUMMARY OF THE INVENTION

According to this invention an artificial leg has upper and lower leg components and a stabilised knee mechanism, the mechanism comprising a hollow brake drum and a brake shoe inside the drum, the drum being connected to one leg component and the shoe being connected to the other leg component, which shoe frictionally engages the inner surface of the drum so as to resist flexion of the leg components when the leg is under load. *The brake shoe comprises a part cylindrical, resilient member wherein the brake shoe is connected to the other of said components so that a toggle joint action is provided in such a manner that relative approaching movement of the components causes the brake shoe to expand inside the drum.* With such a mechanism it is possible to reduce the distance between the knee centre and the lower end of the thigh or other upper leg component. The mechanism, apart from members connecting the brake drum and brake shoe to the leg, may be disposed wholly within the confines of a geometrical cylinder. Thus, in a given available space, a larger drum may be accommodated, and hence a greater friction area may be obtained, than with a mechanism having an external brake band.

Preferably, the mechanism allows the upper and lower leg components to move towards each other when a load is applied to the leg, this movement (known as "compliance") causing the shoe frictionally to engage the drum. The drum may be rigid with the upper leg component and the brake shoe may be a part cylindrical member having an outer friction surface or having a layer of friction lining material attached to its outer surface[, the shoe being pivotally connected to the lower leg component such that relative approaching movement of the leg components causes expansion of the shoe inside the drum and frictional engagement of the lining material with the drum]. *The brake shoe may be pivotally connected to the lower leg component. First, second and third pivot joints are provided such that the first pivot joint is connected at one end of the brake shoe, the second pivot joint is connected at the other end of the brake shoe, and the third pivot joint is mounted on the lower leg component in such a manner that the three pivot joints constitute a toggle joint. Thus, relative approaching movement of the upper and lower leg components causes the first and second pivot joints to be moved apart by the toggle joint to expand the brake shoe inside the brake drum.*

In a preferred embodiment, compliance is provided by pivotally attaching the lower leg component to the outer end of a radius arm member whose inner end is pivotally attached to the upper leg component by a shaft lying in the central axis of the drum, the pivoting axis of the lower leg component and the arm member being parallel to and anterior to the drum axis and, for compactness, within the geometrical cylinder formed by the drum.

To assist disengagement of the drum, release means may be provided. Such release means may comprise one or more compression springs acting for example on the radius arm member to resist the relative approaching movement of the leg components.

DESCRIPTION OF PREFERRED EMBODIMENT

Figure 1:
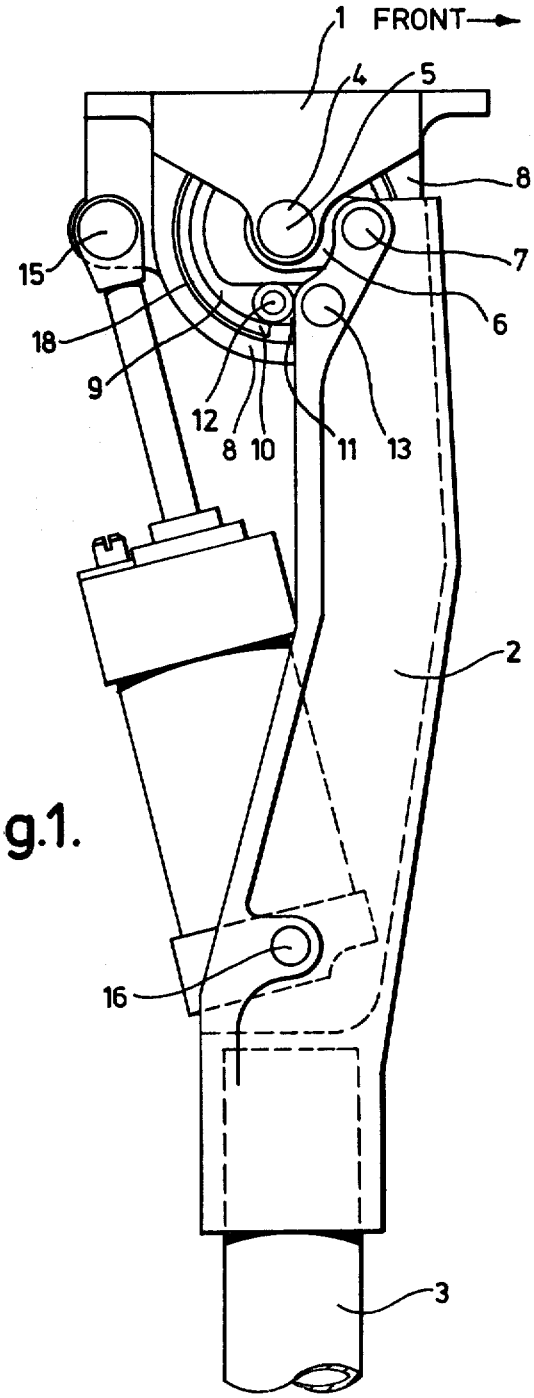
FIG. 1 is a side elevation of part of an artificial leg in accordance with the invention, shown in the position of full extension.

Referring to FIG. 1, there is seen at 1 a knee chassis forming the lower part of one of the leg components, in this case the thigh. A shin cradle 2 is mounted on a tube 3 and forms the upper part of the other leg component, in this case the shin. A shaft 4 is mounted in the chassis 1, the axis of the shaft forming the knee centre 5, and a radius arm member 6 pivots on the shaft 4. The outer end of the radius arm member 6 is pivotaly attached about the axis 7 to the top end of the cradle 2, the member 6 thus connecting the cradle 2 to the chassis 1. Upward movement of the cradle 2 relative to the chassis 1 causes the radius arm member 6 to rotate anti-clockwise about the knee centre 5. The axis 7 is parallel and anterior to the knee centre 5, the front of the leg being to the right as viewed in FIG. 1.

The chassis 1 includes, as an integral part, a hollow brake drum 8 whose axis is coincident with the axis 5 and inside which is mounted a brake shoe 9 with an optional friction lining 10. The shoe 9 is pivotally connected at one end to the cradle 2, being pivotable about the axis 7. The other end of the shoe 9 is connected to the cradle via a pivoting link member 11, which is pivotable relative to the shoe 9 about an axis 12 and relative to the cradle 2 about an axis 13. The artificial leg of FIG. 1 additionally includes a pneumatic swing phase control unit 14, a device which is well-known in the art and the piston and cylinder of which are connected respectively to the chassis 1 at 15 and the shin cradle at 16. This unit 14 also functions in well-known manner as a back-check stop.

Figure 2:
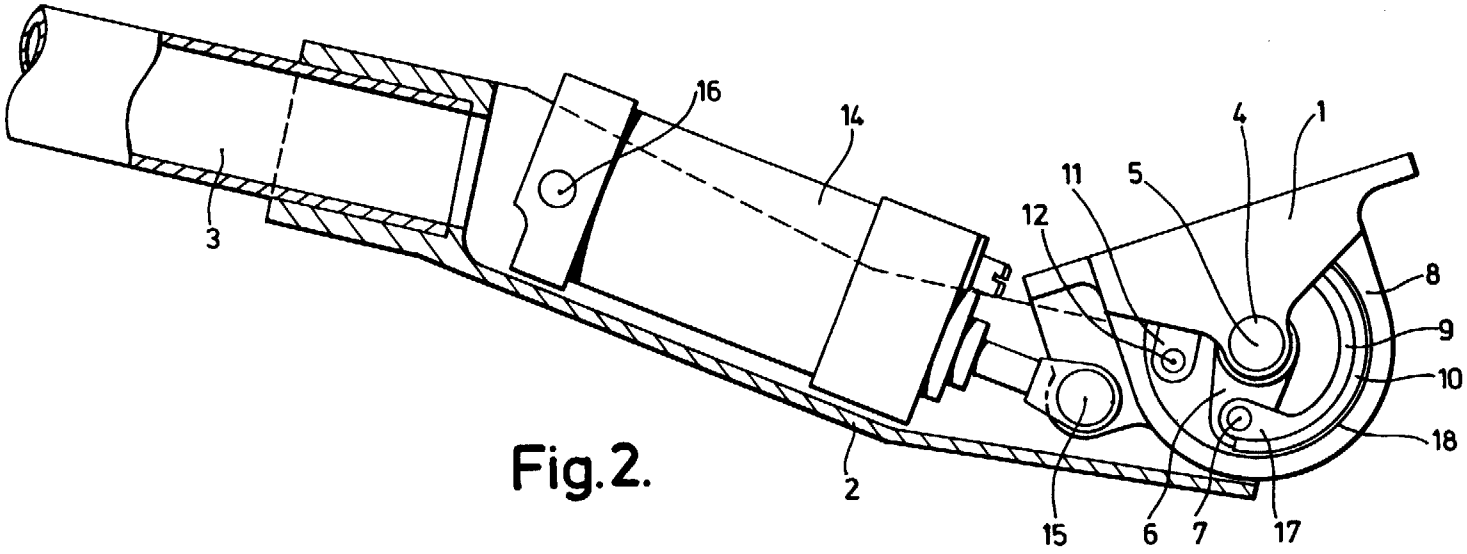
FIG. 2 is a sectional side elevation corresponding to FIG. 1, but showing the leg in the position of full flexion.

FIG. 2 shows the leg of FIG. 1 in the fully flexed position, with the shin cradle 2 sectioned to reveal the ends of the shoe 9.

Referring again to FIG. 1, operation of the knee mechanism is as follows. When a load is applied to the leg, the cradle 2 moves upwards relative to the chassis 1 and causes the radius arm member 6 to rotate anti-clockwise about the knee centre relative to the cradle 2. The upward movement of the axis 7, and therefore also the end portion 17 (FIG. [2] *3*) of the brake shoe 9, forces the shoe to expand and move towards the cylindrical inner surface 18 of the drum 8, since rotation of the shoe 9 relative to the cradle 2 is prevented by the connection of the other end of the shoe 9 to the cradle at 13. Provided that the shin is under thrust, causing the arm member 6 to rotate anti-clockwise about the knee centre 5 relative to the cradle 2, the shoe 9 will frictionally engage the inner surface 18 of the drum 8 so as to resist flexion, whether the leg is extended or flexed.

The braking effect of the knee mechanism during the stance phase therefrom occurs over quite a wide range of knee movement, from extension to considerable flexion (it being understood that the load on the leg varies dring a step).

Figure 3:
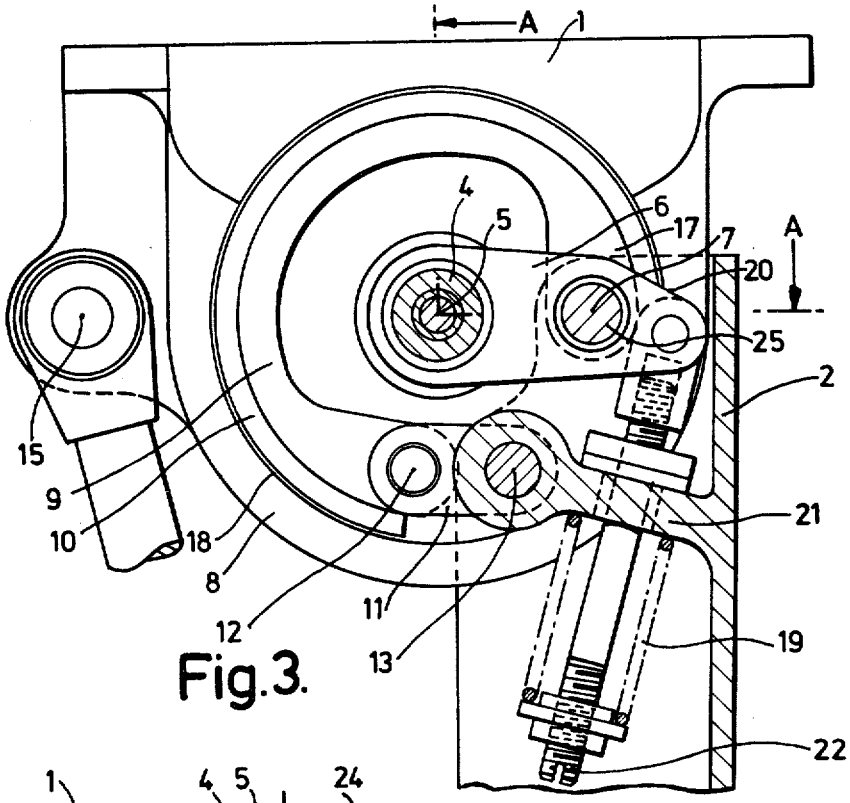
FIG. 3 is an enlarged side elevation of parts of the leg shown in FIG. 1, also showing release means.

To help the amputee to walk naturally it is desirable to provide means for releasing the braking effect at the correct stage in the walking cycle. Referring to FIG. 3, an embodiment of a release device is shown and comprises a compression coil spring 19 acting on an extended portion 20 of the radius arm member 6 and an internal web 21 of the cradle 2 to urge the portion 20 downwards relative to the cradle 2. This has the effect of urging the arm member 6 in a clockwise direction tending to move the chassis 1 away from the cradle 2. Thus the spring 19 opposes the effect of the amputee's weight on the mechanism. An adjustment screw 22 enables the force exerted by the spring 19 on the arm member 6 to be altered. Normally, the screw 22 would be adjusted so that the spring 19 exerts a small residual force when there is no load on the leg. This enables the knee to flex at the correct stage in the walking cycle whilst there is still a small load on the leg. It also enables the amputee to bend the knee as required at other times when there is some weight on the leg, for example, when sitting down.

Figure 4:
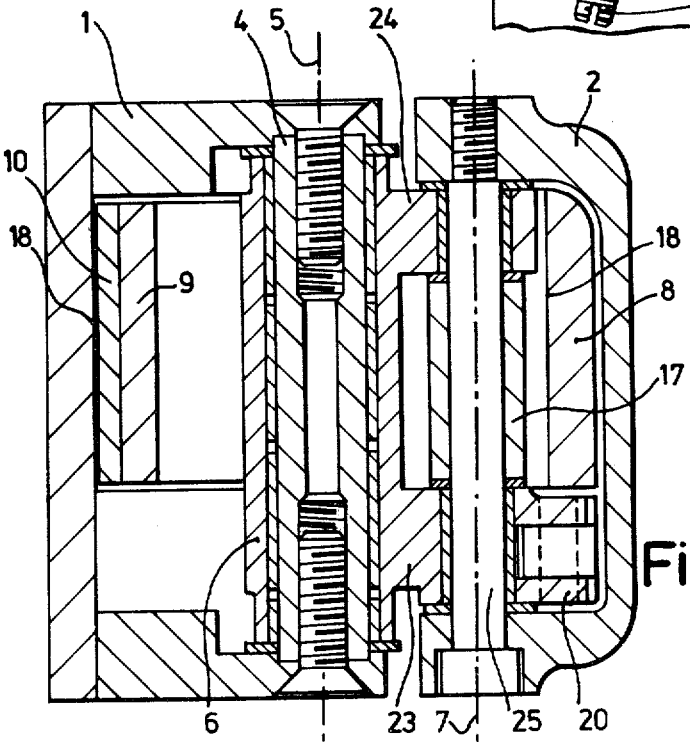
FIG. 4 is a section on the planes indicated by A—A in FIG. 3.

In the sectional view FIG. 4 it can be seen that the radius arm member 6 has two "arms" 23 and 24 embracing the shaft 25, the arm 23 incorporating the extended portion 20 for connection to the spring 19.

Figure 5:
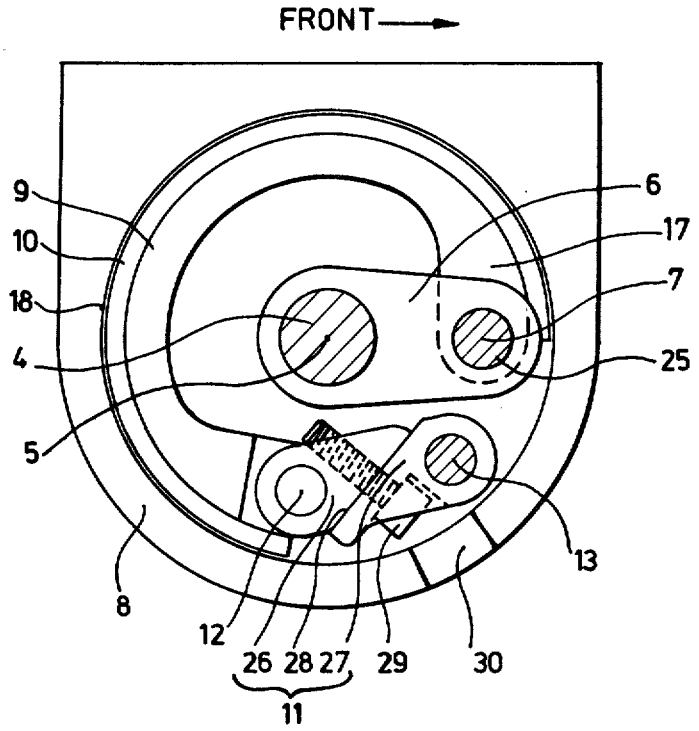
FIG. 5 is an enlarged and simplified side elevation of the drum, brake shoe and radius arm member, showing one embodiment of adjustment means.

FIG. 5 shows an embodiment in which the pivoting link member 11 is adjustable in length. This enables the clearance between the friction lining 10 and the inner surface 18 of the drum 8 to be adjusted when the leg has no load. Thus wear in the friction lining 10 can be taken up. The link member 11 is formed in two parts 26 and 27 meeting in a plane 28. By loosening the adjustment screw 29 the two parts 26 and 27 can be slid relative to each other to adjust the distance between the axes 12 and 13. The opposing faces in the plane 28 are preferably serrated so that the two parts 26 and 27 are securely held together when the screw 29 is tightened. Access to the screw 29 is through a hole 30 in the drum 8. If desired, the link member 11 can be adjusted to give zero clearance for permanent engagement of the lining 10 and the drum 8. This means that the leg will have resistance to flexion in the swing phase as well as in the stance phase, providing a simple form of swing phase control.

We claim:

1. An artificial leg having relatively movable upper and lower components and a stabilised knee mechanism, which mechanism comprises a hollow brake drum and a brake shoe *means* inside the drum *for engaging the inner surface thereof*, the drum being connected to one of the said components and the shoe being connected to the other of the said components, [and means responsive to movement of one of the said components relative to the other of said components, which movement results from application of a load on the leg, the said means causing the] *which brake* shoe *means* frictionally [to engage] *engages* the inner surface of the drum so as to resist flexion of the [knee mechanism] *components when the leg is under load, and which brake shoe means comprises a part-cylindrical, resilient means, the improvement wherein the said brake shoe means is connected to the other of the said components by a toggle joint action in such a manner that relative approaching movement of the said components causes the said brake shoe means to expand inside the said brake drum.*

2. An artificial leg according to claim 1 including release means for assisting disengagement of the *brake* shoe *means* and the drum.

3. An artificial leg according to claim 2 wherein the release means comprises one or more springs urging relative movement apart of the said components.

[4. An artificial leg according to claim 1 wherein the drum is rigidly connected to the upper component and wherein the brake shoe comprises a part cylindrical resilient member pivotally connected to the lower component such that relative movement of one component towards the other causes expansion of the shoe inside the drum and frictional engagement of the shoe with the drum.]

[5. An artificial leg according to claim 4 wherein the lower component is pivotally attached to an outer end portion of a radius arm member about a bearing axis parallel and anterior to the drum axis, the inner end portion of the arm member being pivotally attached to the upper leg component about the drum axis.]

[6. An artificial leg according to claim 5 wherein the bearing axis is within the geometrical cylinder formed by the inner surface of the drum.]

[7. An artificial leg according to claim 4 wherein the brake shoe has two ends which are both individually connected to the lower component, one end being connected via a pivoting link member.]

8. An artificial leg according to claim 1 including means for adjusting the clearance between the *brake* shoe *means* and the drum when the leg is under zero load.

9. An artificial leg according to claim 1 wherein the upper component is a thigh and the lower component is a shin, a fluid swing phase control unit being connected to the shin and thigh.

*10. An artificial leg according to claim 1, wherein the brake shoe means is connected to the said lower component, a first pivot joint being connected at one end of the brake shoe means, a second pivot joint being connected at the other end of the brake shoe means, and a third pivot joint being mounted by the lower component in such manner that the three pivot joints constitute a toggle joint, whereby the relative approaching movement of the said components causes the first and second pivot joints to be moved apart by the toggle joint to expand the brake shoe means inside the brake drum.*

*11. An artificial leg according to claim 10, in which the drum is rigidly connected to the said upper component, and wherein the said lower component is pivotally attached to an outer end portion of a radius arm member at the first pivot joint whose axis is parallel and anterior to the drum axis, the inner end portion of the radius arm member being pivotally attached to the said upper component at the drum axis.*

*12. An artificial leg according to claim 3 further comprising a radius arm member having its outer end portion pivotally attached to the lower component and its inner end portion pivotally attached to the upper component and wherein the release means comprises a compression coil spring bearing at one end against a rod which is connected to the outer end of the radius arm member and at the other end against the said lower component.*

*13. An artificial leg according to claim 10 wherein the first pivot joint is within the geometrical cylinder formed by the inner surface of the brake drum.*

*14. An artificial leg according to claim 1, wherein the two ends of the brake shoe means are separately connected to the said lower component, one of the said two ends being connected to said lower component by a link member which is pivotally connected to said one end and to said lower component.*

*15. An artificial leg according to claim 1 wherein said drum is rigidly connected to one of the said components.*

*16. An artificial leg having relatively movable upper and lower components and a stabilised knee mechanism, which mechanism comprises a hollow drum and a brake shoe means inside the drum for engaging the inner surface thereof, the drum being connected to one of the said components and the shoe being connected to the other of the said components, which brake shoe means frictionally engages the inner surface of the drum so as to resist flexion of the components when the leg is under load, and which brake shoe means comprises a part-cylindrical, resilient means, the improvement wherein the said brake shoe means is connected to the other of the said components by a toggle joint action in such a manner that relative approaching movement of the said components causes the said brake shoe means to expand inside the said drum, and wherein said brake shoe means includes two ends separately connected to said other of the said components, one of said two ends being connected to said other component by a link member which is pivotally connected to said one end and to said other component.*

* * * * *